US012378588B2

United States Patent
Liu et al.

(10) Patent No.: US 12,378,588 B2
(45) Date of Patent: Aug. 5, 2025

(54) TRANSAMINASE MUTANT AND APPLICATION THEREOF IN PREPARATION OF SITAGLIPTIN INTERMEDIATES

(71) Applicants: ZHEJIANG YONGTAI TECHNOLOGY CO., LTD., Zhejiang (CN); ZHEJIANG UNIVERSITY OF TECHNOLOGY, Zhejiang (CN); ZHEJIANG YONGTAI PHARMACEUTICAL CO., LTD., Zhejiang (CN)

(72) Inventors: Zhiqiang Liu, Zhejiang (CN); Feng Cheng, Zhejiang (CN); Xiaojian Zhang, Zhejiang (CN); Dongxu Jia, Zhejiang (CN); Yuguo Zheng, Zhejiang (CN); Renbao He, Zhejiang (CN); Yizhong Jin, Zhejiang (CN); Hongming Shao, Zhejiang (CN); Jiaohua Lin, Zhejiang (CN); Feng Zhang, Zhejiang (CN)

(73) Assignees: ZHEJIANG YONGTAI TECHNOLOGY CO., LTD., Zhejiang (CN); ZHEJIANG UNIVERSITY OF TECHNOLOGY, Zhejiang (CN); ZHEJIANG YONGTAI PHARMACEUTICAL CO., LTD., Zhejiang (CN)

( * ) Notice: Subject to any disclaimer, the term of this patent is extended or adjusted under 35 U.S.C. 154(b) by 515 days.

(21) Appl. No.: 17/778,627

(22) PCT Filed: Jan. 21, 2021

(86) PCT No.: PCT/CN2021/072993
§ 371 (c)(1),
(2) Date: May 20, 2022

(87) PCT Pub. No.: WO2022/088528
PCT Pub. Date: May 5, 2022

(65) Prior Publication Data
US 2022/0396816 A1    Dec. 15, 2022

(30) Foreign Application Priority Data
Oct. 26, 2020    (CN) .......................... 202011158149.4

(51) Int. Cl.
*C12P 17/18*    (2006.01)
*C12N 1/20*    (2006.01)
(Continued)

(52) U.S. Cl.
CPC .............. *C12P 17/182* (2013.01); *C12N 1/20* (2013.01); *C12N 9/1096* (2013.01); *C12N 15/70* (2013.01);
(Continued)

(58) Field of Classification Search
None
See application file for complete search history.

(56) References Cited

FOREIGN PATENT DOCUMENTS

| CN | 108866021 A | 11/2018 |
|----|-------------|---------|
| CN | 111411094 A | 7/2020 |

(Continued)

OTHER PUBLICATIONS

Cheng et al., "Fluorescence-based high-throughput screening system for R-ω-transaminase engineering and its substrate scope extension," Applied Microbiology and Biotechnology, 11 pages.
(Continued)

*Primary Examiner* — Robert B Mondesi
*Assistant Examiner* — Benjamin Hall Easton
(74) *Attorney, Agent, or Firm* — MUNCY, GEISSLER, OLDS & LOWE, P.C.

(57) ABSTRACT

The present invention discloses a transaminase mutant and application thereof in preparation of sitagliptin intermedi-
(Continued)

ates, the transaminase mutant is obtained by substitution of tyrosine with proline at position 74, substitution of glutamic acid with aspartic acid at position 228, substitution of leucine with alanine at position 254 and substitution of methionine with threonine at position 290 of the amino acid sequence shown in SEQ ID NO: 2. The present invention uses wet cells or a purified transaminase as a biocatalyst and a sitagliptin precursor ketone or a prochiral carbonyl compound as a substrate to prepare a sitagliptin intermediate or a sitagliptin ester intermediate; the total yield of the method reaches about 82%, and e.e. value of the product reaches 99%.

9 Claims, 1 Drawing Sheet

Specification includes a Sequence Listing.

(51) Int. Cl.
*C12N 9/10* (2006.01)
*C12N 15/70* (2006.01)

(52) U.S. Cl.
CPC ................ *C12Y 206/01018* (2013.01); *C12N 2800/101* (2013.01)

(56) References Cited

FOREIGN PATENT DOCUMENTS

CN 111534494 A 8/2020
WO WO-2011/026556 A1 3/2011

OTHER PUBLICATIONS

Cheng et al., "ω-Transaminase for asymmetric synthesis of chiral amines and unnatural amino acids," Chinese Journal of Bioprocess Engineering, vol. 16, No. 3, May 2018, 11 pages.

Lu et al., "Mining, functional expression and application of new aminotransferase genes," School of Chemical Engineering and Bioengineering, Zhejiang University, 1 page.

"WP_011781668.1," Multispecies: aminotransferase class IV [Mycolicibacterium], 1 page.

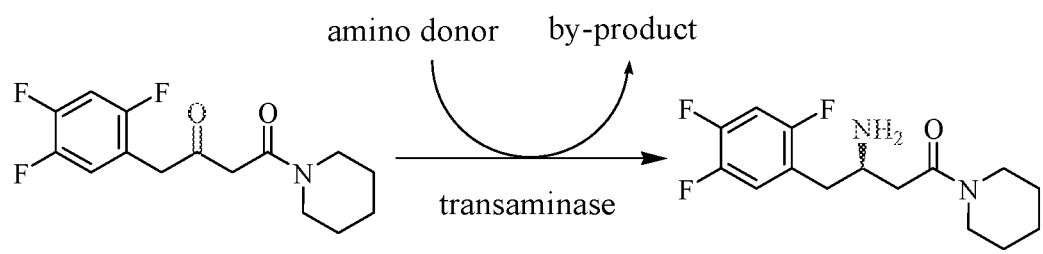

SEQUENCE LISTING

<160> NUMBER OF SEQ ID NOS: 8

<210> SEQ ID NO 1
<211> LENGTH: 1011
<212> TYPE: DNA
<213> ORGANISM: Unknown
<220> FEATURE:
<223> OTHER INFORMATION: Mycobacterium sp. ZJUT007 isolated from soil

<400> SEQUENCE: 1

```
atgggcatcg ataccggtac ttccatcctg gttcatgtcg aagacggcga tgttcgcgag      60
gacaccccgg caggttctgt aatccagtac tctgactacg aaattgatta cagctctccg     120
ttcgccggtg gcgtggcttg gattgaaggc gagtatctgc cggccgagga cgctaaaatt     180
tctgatttcg atacgggttt ttaccattct gacctgacgt acatggtagc tcacgtatgg     240
catggcaaca ttttccgcct gggcgatcac ctggatcgtc tgctggatgg tgcccgtaaa     300
ctgcgcaacg attctggtat gactaaggat gaactggcta catcaccaa aaatgcgtt      360 tctctgtctc agcatttcga agcgtttgtc aacctgacta tcacccgtca ctatggtgat     420
ctgaagggtg agaaagacct gagcaaactg acccatcagg tttatatcta tgcgatcccg     480
gaagtttggg ctttcattcc ggcggaacag atctttggta ccactgccgt tgtgccgcgt     540
catgtgcgcc gcgcaggccg caataccgta gacccgacga tcaagaacta ccaatggggt     600
gatctgaccg cggcgtcttt tgaggccaaa gatcgtggcg cccgtacggc tatcctgatg     660
gatgcggata actgcgtagc cgaaggtccg ggtttcaacg tttgtattgt aaaggtgggc     720
aaactggcat ctccgagcca ctacgctggc ttcggcattc tgcgcaaaac cgttttcgaa     780
attgcaggtg ctatgttcgg tgaggcccat ctgcgtagca ttacttctca cgagctgtat     840
gacgcggacg agattatggc ggtgaccatg ctggatggcg ttactccgat caacactctg     900
gacggtgtac cgattcgcga cggtgttccg ggcccggtta cggttgctat tcgcgaccgt     960
ttctgggctc tgatggacga gccgtacccg gtgatcgaag atatctgcta c             1011
```

<210> SEQ ID NO 2
<211> LENGTH: 337
<212> TYPE: PRT
<213> ORGANISM: Unknown
<220> FEATURE:
<223> OTHER INFORMATION: Mycobacterium sp. ZJUT007 isolated from soil

<400> SEQUENCE: 2

```
Met Gly Ile Asp Thr Gly Thr Ser Ile Leu Val His Val Glu Asp Gly
  1               5                  10                  15

Asp Val Arg Glu Asp Thr Pro Ala Gly Ser Val Ile Gln Tyr Ser Asp
             20                  25                  30

Tyr Glu Ile Asp Tyr Ser Ser Pro Phe Ala Gly Gly Val Ala Trp Ile
         35                  40                  45

Glu Gly Glu Tyr Leu Pro Ala Gly Asp Ala Lys Ile Ser Asp Phe Asp
     50                  55                  60

Thr Gly Phe Tyr His Ser Asp Leu Thr Tyr Met Val Ala His Val Trp
 65                  70                  75                  80
```

His Gly Asn Ile Phe Arg Leu Gly Asp His Leu Asp Arg Leu Leu Asp
             85                  90                  95

Gly Ala Arg Lys Leu Arg Asn Asp Ser Gly Met Thr Lys Asp Glu Leu
        100                 105                 110

Ala Asp Ile Thr Lys Lys Cys Val Ser Leu Ser Gln His Phe Glu Ala
        115                 120                 125

Phe Val Asn Leu Thr Ile Thr Arg His Tyr Gly Asp Leu Lys Gly Glu
        130                 135                 140

Lys Asp Leu Ser Lys Leu Thr His Gln Val Tyr Ile Tyr Ala Ile Pro
145                 150                 155                 160

Glu Val Trp Ala Phe Ile Pro Ala Glu Gln Ile Phe Gly Thr Thr Ala
                165                 170                 175

Val Val Pro Arg His Val Arg Arg Ala Gly Arg Asn Thr Val Asp Pro
                180                 185                 190

Thr Ile Lys Asn Tyr Gln Trp Gly Asp Leu Thr Ala Ala Ser Phe Glu
            195                 200                 205

Ala Lys Asp Arg Gly Ala Arg Thr Ala Ile Leu Met Asp Ala Asp Asn
        210                 215                 220

Cys Val Ala Glu Gly Pro Gly Phe Asn Val Cys Ile Val Lys Val Gly
225                 230                 235                 240

Lys Leu Ala Ser Pro Ser His Tyr Ala Gly Phe Gly Ile Leu Arg Lys
                245                 250                 255

Thr Val Phe Glu Ile Ala Gly Ala Met Phe Gly Glu Ala His Leu Arg
                260                 265                 270

Ser Ile Thr Ser His Glu Leu Tyr Asp Ala Asp Glu Ile Met Ala Val
            275                 280                 285

Thr Met Leu Asp Gly Val Thr Pro Ile Asn Thr Leu Asp Gly Val Pro
        290                 295                 300

Ile Arg Asp Gly Val Pro Gly Pro Val Thr Val Ala Ile Arg Asp Arg
305                 310                 315                 320

Phe Trp Ala Leu Met Asp Glu Pro Tyr Pro Val Ile Glu Asp Ile Cys
                325                 330                 335

Tyr

<210> SEQ ID NO 3
<211> LENGTH: 1011
<212> TYPE: DNA
<213> ORGANISM: Artificial Sequence
<220> FEATURE:
<223> OTHER INFORMATION: transaminase mutant

<400> SEQUENCE: 3
atgggcatcg ataccggtac ttccatcctg gttcatgtcg aagacggcga tgttcgcgag      60
gacaccccgg caggttctgt aatccagtac tctgactacg aaattgatta cagctctccg     120
ttcgccggtg gcgtggcttg gattgaaggc gagtatctgc cggccgagga cgctaaaatt     180
tctgatttcg atacgggttt ttaccattct gacctgacgc ccatggtagc tcacgtatgg     240
catggcaaca ttttccgcct gggcgatcac ctggatcgtc tgctggatgg tgcccgtaaa     300
ctgcgcaacg attctggtat gactaaggat gaactggctg acatcaccaa aaaatgcgtt     360
tctctgtctc agcatttcga agcgtttgtc aacctgacta tcacccgtca ctatggtgat     420
ctgaagggtg agaaagacct gagcaaactg acccatcagg tttatatcta tgcgatcccg     480
gaagtttggg ctttcattcc ggcggaacag atctttggta ccactgccgt tgtgccgcgt     540
catgtgcgcc gcgcaggccg caataccgta gacccgacga tcaagaacta ccaatgggt      600

```
gatctgaccg cggcgtctit tgaggccaaa gatcgtggcg cccgtacggc tatcctgatg    660
gatgcggata actgcgtagc cgatggtccg ggtttcaacg tttgtattgt aaaggtgggc    720
aaactggcat ctccgagcca ctacgctggc ttcggcattg cgcgcaaaac cgttttcgaa    780
attgcaggtg ctatgttcgg tgaggcccat ctgcgtagca ttacttctca cgagctgtat    840
gacgcggacg agattatggc ggtgaccacg ctggatggcg ttactccgat caacactctg    900
gacggtgtac cgattcgcga cggtgttccg ggcccggtta cggttgctat tcgcgaccgt    960
ttctgggctc tgatggacga gccgtacccg gtgatcgaag atatctgcta c            1011
```

<210> SEQ ID NO 4
<211> LENGTH: 337
<212> TYPE: PRT
<213> ORGANISM: Artificial Sequence
<220> FEATURE:
<223> OTHER INFORMATION: transaminase mutant

<400> SEQUENCE: 4

```
Met Gly Ile Asp Thr Gly Thr Ser Ile Leu Val His Val Glu Asp Gly
1               5                   10                  15

Asp Val Arg Glu Asp Thr Pro Ala Gly Ser Val Ile Gln Tyr Ser Asp
            20                  25                  30

Tyr Glu Ile Asp Tyr Ser Ser Pro Phe Ala Gly Gly Val Ala Trp Ile
        35                  40                  45

Glu Gly Glu Tyr Leu Pro Ala Glu Asp Ala Lys Ile Ser Asp Phe Asp
    50                  55                  60

Thr Gly Phe Tyr His Ser Asp Leu Thr Pro Met Val Ala His Val Trp
65                  70                  75                  80

His Gly Asn Ile Phe Arg Leu Gly Asp His Leu Asp Arg Leu Leu Asp
                85                  90                  95

Gly Ala Arg Lys Leu Arg Asn Asp Ser Gly Met Thr Lys Asp Glu Leu
            100                 105                 110

Ala Asp Ile Thr Lys Lys Cys Val Ser Leu Ser Gln His Phe Glu Ala
        115                 120                 125

Phe Val Asn Leu Thr Ile Thr Arg His Tyr Gly Asp Leu Lys Gly Glu
    130                 135                 140

Lys Asp Leu Ser Lys Leu Thr His Gln Val Tyr Ile Tyr Ala Ile Pro
145                 150                 155                 160

Glu Val Trp Ala Phe Ile Pro Ala Glu Gln Ile Phe Gly Thr Thr Ala
                165                 170                 175

Val Val Pro Arg His Val Arg Arg Ala Gly Arg Asn Thr Val Asp Pro
            180                 185                 190

Thr Ile Lys Asn Tyr Gln Trp Gly Asp Leu Thr Ala Ala Ser Phe Glu
        195                 200                 205

Ala Lys Asp Arg Gly Ala Arg Thr Ala Ile Leu Met Asp Ala Asp Asn
    210                 215                 220

Cys Val Ala Asp Gly Pro Gly Phe Asn Val Cys Ile Val Lys Val Gly
225                 230                 235                 240

Lys Leu Ala Ser Pro Ser His Tyr Ala Gly Phe Gly Ile Ala Arg Lys
                245                 250                 255

Thr Val Phe Glu Ile Ala Gly Ala Met Phe Gly Glu Ala His Leu Arg
            260                 265                 270

Ser Ile Thr Ser His Glu Leu Tyr Asp Ala Asp Glu Ile Met Ala Val
        275                 280                 285
```

```
Thr Thr Leu Asp Gly Val Thr Pro Ile Asn Thr Leu Asp Gly Val Pro
    290                 295                 300

Ile Arg Asp Gly Val Pro Gly Pro Val Thr Val Ala Ile Arg Asp Arg
305                 310                 315                 320

Phe Trp Ala Leu Met Asp Glu Pro Tyr Pro Val Ile Glu Asp Ile Cys
                325                 330                 335

Tyr

<210> SEQ ID NO 5
<211> LENGTH: 15
<212> TYPE: DNA
<213> ORGANISM: Artificial Sequence
<220> FEATURE:
<223> OTHER INFORMATION: primer 1

<400> SEQUENCE: 5
atgggcatcg atacc                                                       15

<210> SEQ ID NO 6
<211> LENGTH: 17
<212> TYPE: DNA
<213> ORGANISM: Artificial Sequence
<220> FEATURE:
<223> OTHER INFORMATION: primer 2

<400> SEQUENCE: 6
gtagcagata tcttcga                                                     17

<210> SEQ ID NO 7
<211> LENGTH: 29
<212> TYPE: DNA
<213> ORGANISM: Artificial Sequence
<220> FEATURE:
<223> OTHER INFORMATION: primer 3

<400> SEQUENCE: 7
ccggaattcg gtatcgacac cggtacctc                                        29

<210> SEQ ID NO 8
<211> LENGTH: 31
<212> TYPE: DNA
<213> ORGANISM: Artificial Sequence
<220> FEATURE:
<223> OTHER INFORMATION: primer 4

<400> SEQUENCE: 8
ttgggatccg tactggatag cttcgatcag c                                     31
```

TRANSAMINASE MUTANT AND APPLICATION THEREOF IN PREPARATION OF SITAGLIPTIN INTERMEDIATES

TECHNICAL FIELD

The present invention relates to the technical field of biochemical industry, in particular to a method for preparing optically pure sitagliptin intermediates through a transaminase and its mutant enzyme, including the transaminase, the mutant, their encoding genes, a recombinant vector containing the gene, a recombinant genetically engineered strain and a recombinase obtained by transformation of the recombinant vector, and application thereof.

BACKGROUND ART

Sitagliptin, developed by Merck and Codexis of the United States, is the first dipeptidyl peptidase-IV (DPP-IV) inhibitor approved by the FDA for treatment of type II diabetes. Sitagliptin can enhance insulin secretion in a glucose-dependent manner, has a moderate hypoglycemic effect without causing hypoglycemia, and has no side effects such as weight gain, nausea and vomiting. The trade name of sitagliptin is Januvia, which has been approved for use in more than 70 countries around the world, and is one of the top 20 drug sales in the world.

Sitagliptin and its intermediates can be prepared by chemo-enzymatic method which has gradually become the first choice for the synthesis of chiral pharmaceutical chemicals and their intermediates. The key to the chemo-enzymatic method is to obtain a transaminase that can catalyze asymmetric transamination reaction to obtain optically pure sitagliptin intermediates. U.S. Pat. No. 8,293,507 discloses a biocatalyst obtained by modification of Arthrobacter-derived transaminase (ATA117) by Codexis Company, and ee value of its transamination product reaches 99%.

However, to date, there are few reports on natural transaminases with (R)-selectivity, and the substrate spectrum catalyzed by these transaminases is relatively narrow, and they are often the most suitable biocatalysts for specific reactions. Therefore, their application scope is greatly limited, and few of them can be used in synthesis of sitagliptin intermediates. With development of directed evolution technology, protein engineering is increasingly used to modify substrate specificity of enzymes. To screen novel transaminases with broad substrate spectrum and to study chiral drugs and their intermediates that can be catalyzed by the enzymes with high efficiency and high selectivity, can not only broaden their application scope and enhance their application potential, but also lay a foundation for realizing industrial production.

SUMMARY OF THE INVENTION

Aiming at the defects existing in the existing process for producing sitagliptin intermediates (such as poor stereoselectivity, expensive catalysts, difficult solvent recovery, etc.), the present invention provides a transaminase mutant, an encoding gene, a recombinant vector, a recombinant genetically engineered strain and application thereof in preparation of sitagliptin or sitagliptin ester intermediates by asymmetric transamination which has high raw material conversion rate, low production cost and high yield.

The present invention adopts technical solutions as follows:

The present invention provides a transaminase mutant, wherein the transaminase mutant is obtained by substitution of tyrosine with proline at position 74, substitution of glutamic acid with aspartic acid at position 228, substitution of leucine with alanine at position 254 and substitution of methionine with threonine at position 290 of the amino acid sequence shown in SEQ ID NO: 2, and the amino acid sequence of the transaminase mutant is shown in SEQ ID NO: 4, and the nucleotide sequence of the encoding gene is shown in SEQ ID NO: 3.

The transaminase mutant of the present invention is obtained by mutating a transaminase derived from *Mycolicibacterium*, the amino acid sequence of the transaminase is shown in SEQ ID NO: 2, and the nucleotide sequence is shown in SEQ ID NO: 1. The amino acid sequence of the transaminase shown in SEQ ID No: 2 of the present invention is only 42% identical to *Arthrobacter*-derived transaminase ATA117-Rd11 (U.S. Pat. No. 8,293,507), which shows significant difference.

The present invention also relates to a recombinant vector constructed from an encoding gene of the transaminase mutant and recombinant genetically engineered bacteria obtained by transformation of the recombinant vector, and the recombinant genetically engineered bacteria are preferably prepared as follows: the transaminase gene (or the transaminase mutant gene) is connected with the expression vector pET28b to construct a heterologous recombinant expression plasmid pET28b-MbTA (or pET28b-MbTAmut1) containing the transaminase gene; and the recombinant expression plasmid pET28b-MbTA (or pET28b-MbTAmut1) is introduced into *Escherichia coli* BL21 (DE3) to obtain the recombinant *E. coli* containing the recombinant plasmid pET28b-MbTA (or pET28b-MbTAmut1).

The present invention also provides an application of the transaminase mutant in synthesizing a sitagliptin intermediate with a sitagliptin precursor ketone by biocatalysis, and the application is carried out as follows: wet cells or a purified transaminase as a biocatalyst, the sitagliptin precursor ketone ([1-piperidinyl]-4-[2,4,5-trifluorophenyl]-1,3-butanedione) as a substrate, dimethyl sulfoxide(DMSO) as a cosolvent, pyridoxal phosphate as a coenzyme, isopropyl amine as a cosubstrate, and a pH 8-9 triethanolamine buffer as a reaction medium are used to construct a reaction system, a biocatalytic reaction is carried out at 30-45° C. (preferably 35° C.) and 100-250 r/min(preferably 150 r/min), after the reaction is completed, the reaction solution is subjected to separation and purification to obtain the sitagliptin intermediate ((R)-3-amino-1-(1-piperidinyl)-4-(2,4,5-trifluorophenyl)-1-butanone); in which, the wet wells are obtained by fermentation culture of the recombinant genetically engineered bacteria (preferably recombinant *E. coli*) containing the encoding gene of the transaminase mutant, and the purified transaminase is obtained by subjecting the wet cells to ultrasonication and then extraction; in the reaction system, the amount of the wet cells is 10~50 g/L(preferably 50 g/L), the amount of the purified transaminase is 0.01-1.0 g/L (preferably 0.07 g/L), the final concentration of the substrate is 2~50 g/L(preferably 20 g/L), the final concentration of dimethyl sulfoxide is 10-40% (v/v)(preferably 20%), the final concentration of pyridoxal phosphate is 0.5 g/L, and the final concentration of isopropyl amine is 10 g/L.

The present invention also provides an application of the transaminase mutant in synthesizing a sitagliptin ester intermediate with a prochiral carbonyl compound by biocatalysis, and the application is carried out as follows: wet cells as a biocatalyst, the prochiral carbonyl compound as a substrate, dimethyl sulfoxide (DMSO) as a cosolvent, pyridoxal phosphate as a coenzyme, isopropyl amine as a cosubstrate, and a pH 8-9 triethanolamine buffer as a reaction medium are used to construct a reaction system, a biocatalytic reaction is carried out at 25-35° C. (preferably 35° C.) and 100-250 r/min(preferably 150 r/min), after the reaction is completed, the reaction solution is subjected to separation and purification to obtain the sitagliptin ester intermediate; in which, the wet wells are obtained by fermentation culture of the recombinant genetically engineered bacteria (preferably recombinant E. coli) containing the encoding gene of the transaminase mutant; in the reaction system, the amount of the wet cells is 10~100 g/L (preferably 50 g/L), the final concentration of the substrate is 2~60 g/L (preferably 20 g/L), the final concentration of dimethyl sulfoxide is 10-40% (v/v)(preferably 20%), the final concentration of pyridoxal phosphate is 0.5 g/L, and the final concentration of isopropyl amine is 10 g/L; the substrate is one selected from the group consisting of the following compounds: 3-carbonyl-4-(2,4,5-trifluorophenyl)-butyric acid methyl ester, 3-carbonyl-4-(2,4,5-Trifluorophenyl)-butyric acid propyl ester, 3-carbonyl-4-(2,4,5-trifluorophenyl)-butyric acid isopropyl ester, 3-carbonyl-4-(2,4,5-trifluorophenyl)-butyric acid ethyl ester, 3-carbonyl-4-(2,4,5-trifluorophenyl)-butyric acid isobutyl ester and 3-carbonyl-4-(2,4,5-trifluorophenyl)-butyric acid benzyl ester.

In the present invention, a method for separating and purifying (R)-3-amino-1-(1-piperidinyl)-4-(2,4,5-trifluorophenyl)-1-butanone from the reaction solution is carried out as follows: after the reaction is completed, the pH of the reaction solution is adjusted to 1.0-2.0 with concentrated hydrochloric acid (the mass fraction is 36%-38%), diatomaceous earth is added to adsorb cells, the resulting mixture is stirred for 10-30 min and filtered to obtain filtrate a and filtration residue a; 1M hydrochloric acid (the amount is enough to immerge the filtration residue a, preferably the volume ratio of the hydrochloric acid and the reaction solution is 1.5:1) is added to the filtration residue a and stirred for 10-30 min, the mixture is subjected to suction filtration to obtain filtrate b and filtration residue b; the filtrate a is mixed with the filtrate b, the mixed filtrate is subjected to extraction once with dichloromethane to obtain organic phase a and aqueous phase a, the organic phase a is subjected to extraction with 1M hydrochloric acid to obtain organic phase b and aqueous phase b, the aqueous phase a is mixed with the aqueous phase b, the pH of the mixed aqueous phase is adjusted to 12 with sodium hydroxide, then the mixed aqueous phase is subjected to extraction with dichloromethane to obtain organic phase c and aqueous phase c, dichloromethane is added to the aqueous phase c for extraction to obtain organic phase d and aqueous phase d, the organic phase c is mixed with the organic phase d and the mixed organic phase is washed twice with a saturated sodium chloride aqueous solution, anhydrous sodium sulfate is added to dry the mixed organic phase, the mixed organic phase is subjected to suction filtration to remove sodium sulfate, and then the dried organic phase is subjected to rotary evaporation at 45° C., thereby obtaining the sitagliptin intermediate; in which, the amount of the diatomaceous earth calculated by the volume of the reaction solution is 0.18 g/mL. Take 400 mL of the reaction solution as an example: I. the pH of the reaction solution is adjusted to 1.5 with concentrated hydrochloric acid (the mass fraction is 36%-38%), 72 g of diatomaceous earth is added to adsorb cells and the resulting mixture is stirred for 20 min, the mixture is filtered to obtain filtrate a and filtration residue a; 600 mL of 1M hydrochloric acid is added to the filtration residue a and stirred for 20 min, the mixture is subjected to suction filtration to obtain filtrate b and filtration residue b; II. the filtrate a is mixed with the filtrate b (the total volume is about 1.0 L), the mixed filtrate is subjected to extraction once with 500 mL of dichloromethane to obtain organic phase a and aqueous phase a, the organic phase a is subjected to extraction with 100 mL of 1M hydrochloric acid to obtain organic phase b and aqueous phase b, the aqueous phase a is mixed with the aqueous phase b, the pH of the mixed aqueous phase is adjusted to 12 with sodium hydroxide, then the mixed aqueous phase is subjected to extraction with 1.2 L of dichloromethane to obtain organic phase c and aqueous phase c, 800 mL of dichloromethane is added to the aqueous phase c for extraction to obtain organic phase d and aqueous phase d, the organic phase c is mixed with the organic phase d; III. the mixed organic phase is washed twice with a saturated sodium chloride aqueous solution (36 g/L), anhydrous sodium sulfate is added to dry the mixed organic phase, the mixed organic phase is subjected to suction filtration to remove sodium sulfate, and the dried organic phase is subjected to rotary evaporation at 45° C., thereby obtaining 23.1 g of the sitagliptin intermediate (white powder), whose purification yield is 95% and purity is more than 99%. The letters a, b, c and d in the filtrate a, the filtrate b, the filtration residue a, the filtration residue b, the organic phase a, the organic phase b, the organic phase c, the organic phase d, the aqueous phase a, the aqueous phase b, the aqueous phase c and the aqueous phase d of the present invention have no special meanings and are only named for convenience of description.

The wet cells of the present invention are prepared as follows: the recombinant Escherichia coli strain containing the encoding gene of the transaminase or the transaminase mutant is inoculated into LB liquid medium containing 50 μg/ml kanamycin, cultured at 37° C. and 200 rpm for 12 hours, the resulting inoculum is inoculated into fresh LB liquid medium containing 50 μg/ml kanamycin with 1% incubating volume and cultured at 37° C. and 150 rpm; when OD600 of the cells reaches 0.6-0.8, IPTG is added with the final concentration of 0.1 mM, and the bacteria solution is subjected to induction culture at 28° C. for 12 hours; the resulting solution is subjected to centrifugation at 4° C. and 5000 rpm for 20 min, the resulting supernatant is discarded and sediment is collected, thereby obtaining the wet cells.

The method for extracting the purified transaminase from the wet cells of the present invention after ultrasonication is carried out as follows: the wet cells are resuspended in a binding buffer (a 50 mM, pH 8.0 sodium phosphate buffer containing 300 mM NaCl and 10 mM imidazole) and subjected to ultrasonication for cell disruption (in an ice bath, 240 W for 10 min, 2 s breaking, 2 s pause), the broken product is subjected to centrifugation at 12000 rpm for 40 min, the resulting supernatant is incubated with Ni affinity chromatography resin which has been equilibrated with the above-mentioned binding buffer, the resulting Ni affinity chromatography resin is washed with a washing buffer (a 50 mM, pH 8.0 sodium phosphate buffer containing 300 mM NaCl and 20 mM imidazole) until there are substantially no protein impurities, and then eluted with an elution buffer (a 50 mM, pH 8.0 sodium phosphate buffer, containing 300 mM NaCl and 250 mM imidazole), and the resulting eluate is collected to obtain solutions containing the target protein, the purity of the target protein is identified by electrophoresis, and the solutions containing the target protein are combined and dialyzed with a dialysis buffer (a 50 mM, pH 8.0 sodium phosphate buffer) for 48 h (the MWCO of the dialysis bag is 14l(D), and the retention is collected to obtain the purified transaminase.

A protein with transaminase activity which is obtained by substitution, deletion or insertion of one or more amino acid residues in the amino acid sequences of the present invention and is at least 95% identical to the amino acid sequences of the present invention, belongs to the protection scope of the present invention. The protein whose amino acid sequence is shown in SEQ ID No: 2 can be isolated and obtained from *Mycobacterium* or an expression transformant that recombinantly expresses the protein, or can be obtained by artificial synthesis. The identity between two amino acid sequences or two nucleotide sequences can be obtained by algorithms which are commonly used in the art, preferably calculated by NCBI Blastp and Blastn softwares with default parameters.

As known to a person skilled in the art, due to degeneracy of codons, the nucleic acid sequences encoding the amino acid sequences shown in SEQ ID No:2 and SEQ ID No:4 are not limited to SEQ ID No:1 and SEQ ID No:3. The transaminase gene of the present invention may also be a homolog of a polynucleotide obtained by appropriately introducing substitution(s), deletion(s), or insertion(s) to SEQ ID No:1 or SEQ ID No:3.

The present invention also relates to an application of the transaminase gene in preparation of a recombinant transaminase, specifically, the application is carried out as follows: a recombinant vector containing the transaminase gene (or the transaminase mutant gene) is constructed and transformed into *Escherichia coli*, the resulting recombinant genetically engineered bacteria are subjected to induction culture, and the culture medium is separated to obtain bacterial cells containing the recombinant transaminase, the bacterial cells are subjected to cell disruption to obtain a crude transaminase solution, and the crude transaminase solution is subjected to purification to obtain the purified recombinant transaminase (or transaminase mutant).

The catalyst of the present invention can be used in various forms, such as pure transaminase and mutant thereof, the corresponding wet cells of recombinant genetically engineered bacteria, crude enzyme solution, crude enzyme powder, pure enzyme solution, pure enzyme powder, etc.

The present invention provides an application of the transaminase in synthesizing a sitagliptin intermediate by biocatalysis, and the application is carried out as follows: wet cells as a biocatalyst, the sitagliptin precursor ketone ([1-piperidinyl]-4-[2,4,5-trifluorophenyl]-1,3-butanedione) as a substrate, dimethyl sulfoxide (DMSO) as a cosolvent, pyridoxal phosphate as a coenzyme, isopropyl amine as a cosubstrate, and a pH 8-9 triethanolamine buffer are used as a reaction medium to construct a reaction system, the biocatalytic reaction is carried out at 30-45° C. and 100-250 r/min, after the reaction is completed, the reaction solution is subjected to separation and purification to obtain the sitagliptin intermediate ((R)-3-amino-1-(1-piperidinyl)-4-(2,4,5-trifluorophenyl)-1-butanone); in which, the wet wells are obtained by fermentation culture of the recombinant *Escherichia coli* strain containing the encoding gene of the transaminase; in the reaction system, the amount of the wet cells is 10~50 g/L (preferably 50 g/L), the final concentration of the substrate is 2~50 g/L, the final concentration of dimethyl sulfoxide is 10-20% (v/v), the final concentration of pyridoxal phosphate is 0.5 g/L, and the final concentration of isopropyl amine is 10 g/L.

Compared with prior art, advantages of the present invention are mainly embodied in: Aiming at the problems that total yields of reported asymmetric synthesis of sitagliptin and its intermediates are not high (generally lower than 50%), that stereoselectivity is low (the e.e. value of the product is generally lower than 90%), that metal catalysts are expensive, and that the existing bio catalysts cannot directly use the sitagliptin precursor ketone as a substrate, the present invention provides a transaminase mutant (biocatalyst) derived from *Mycolicibacterium*, and uses a sitagliptin precursor ketone (ie. [1-piperidinyl]-4-[2,4,5-trifluorophenyl]-1,3-butanedione) or a sitagliptin ester intermediate carbonyl compound (3-carbonyl-4-(2,4,5-trifluorophenyl)-butyric acid methyl ester, 3-carbonyl-4-(2,4,5-Trifluorophenyl)-butyric acid propyl ester, 3-carbonyl-4-(2,4,5-trifluorophenyl)-butyric acid isopropyl ester, 3-carbonyl-4-(2,4,5-trifluorophenyl)-butyric acid ethyl ester, 3-carbonyl-4-(2,4,5-trifluorophenyl)-butyric acid isobutyl ester or 3-carbonyl-4-(2,4,5-trifluorophenyl)-butyric acid benzyl ester) as a substrate, isopropyl amine as an amino donor and pyridoxal phosphate as a coenzyme to carry out the biocatalytic reaction, and then carry out separation and purification to obtain sitagliptin intermediates or sitagliptin ester intermediates with high optical purity. The total yield of the method reaches 82% (including conversion yield and separation and purification yield), and e.e. value of the product reaches 99% (high stereoselectivity).

BRIEF DESCRIPTION OF THE DRAWINGS

The sole FIGURE is a schematic diagram of biocatalytic reactions for synthesis of sitagliptin intermediates by transaminase mutants.

SPECIFIC EMBODIMENTS

The present invention is further illustrated below with specific examples, but the protection scope of the present invention is not limited thereto:

Example 1: Amplification of Transaminase Gene MbTA

According to sequencing information of transaminase gene from *Mycobacterium* collected by GenBank, the total genomic DNA of *Mycobacterium* was extracted in a fast nucleic acid extraction apparatus. The genomic DNA was used as a template to carry out PCR amplification with primer 1 (ATGGGCATCGATACC, SEQ ID NO: 5) and primer 2 (GTAGCAGATATCTTCGA, SEQ ID NO: 6). The PCR reaction mixture (total volume 50 μL) was composed of 5 μL of 10×Pfu DNA Polymerase Buffer, 1 μL of 10 mM dNTP mixture (dATP, dCTP, dGTP and dTTP each 2.5 mM), 1 μL of each of 50 μM cloning primer 1 and 50 μM cloning primer 2, 1 μL of the genomic DNA, 14, of Pfu DNA Polymerase and 40 μL of nucleic acid-free water.

A BioRad PCR instrument was used. The PCR reaction conditions were as follows: pre-denaturation at 95° C. for 5 min, a total of 30 cycles of denaturation at 95° C. for 30 s, annealing at 65° C. for 45 s and extension at 72° C. for 1 min, and a final extension at 72° C. for 10 min.

The PCR reaction solution was detected by 0.9% agarose gel electrophoresis, and the desired DNA band was cut from the gel and purified. Base A was introduced into the 5'-terminus of the fragment with Taq DNA polymerase. The resulting fragment was ligated into a pMD18-T vector with T4 DNA ligase, thereby obtaining a cloned recombinant plasmid pMD18-T-MbTA. The recombinant plasmid was transformed into *Escherichia coli* JM109 and screened by blue-white screening, and white clones were randomly selected for sequencing, and the sequencing results were analyzed by software. The results showed that the length of the nucleotide sequence amplified by primer 1 and primer 2 was 1011 bp (MbTA gene, the nucleotide sequence is shown in SEQ ID NO: 1, and the amino acid sequence of the encoded protein is shown in SEQ ID NO: 2), which encodes a complete open reading frame.

Example 2: Construction of Recombinant *Escherichia coli* BL21/pET28b-MbTA

Primer 3 (CCGGAATTC GGTATCGACACCGG-TACCTC, SEQ ID NO: 7) and primer 4 (TTGGGATCC GTACTGGATAGCTTCGATCAGC, SEQ ID NO: 8) were designed according to the MbTA gene sequence in Example 1, and EcoR I and BamH I restriction sites (underlined) were introduced into primer 3 and primer 4, respectively. Under the initiation of primer 3 and primer 4, high-fidelity Pfu DNA polymerase was used for amplification, and the recombinant plasmid pMD18-T-MbTA was used as a template (obtained in Example 1) to obtain the MbTA gene sequence. After sequencing, restriction endonucleases (TaKaRa) EcoR I and BamH I were used to treat the amplified fragment, and the fragment was ligated with a commercial vector pET28b (Invitrogen) which had been treated with the same restriction endonucleases with T4 DNA ligase (TaKaRa) to construct an expression vector pET28b-MbTA. The constructed expression vector pET28b-MbTA was transformed into *E. coli* BL21(DE3) (Invitrogen) (42° C., 90 s), spreaded onto an LB plate containing 50 μg/ml kanamycin, and cultured at 37° C. for 8-12 h. The resulting monoclones were randomly picked and subjected to plasmid extraction for sequencing, identification and screening, thereby obtaining recombinant *Escherichia coli* BL21(DE3)/pET28b-MbTA containing the recombinant expression plasmid pET28b-MbTA.

Example 3: Induction Expression of Transaminase (MbTA)

The recombinant *Escherichia coli* BL21(DE3)/pET28b-MbTA obtained in Example 2 was inoculated into LB liquid medium containing 50 μg/ml kanamycin and cultured at 37° C. and 200 rpm for 12 h, the resulting inoculum was inoculated into fresh LB liquid medium containing 50 μg/ml kanamycin with 1% (v/v) incubating volume and cultured at 37° C. and 150 rpm; when OD600 of the cells reached 0.6-0.8, IPTG was added with the final concentration of 0.1 mM, and the bacteria solution was subjected to induction culture at 28° C. for 12 hours; the resulting solution was subjected to centrifugation at 4° C. and 5000 rpm for 25 min, the resulting supernatant was discarded and sediment was collected, thereby obtaining wet cells of the recombinant *Escherichia coli* BL21(DE3)/pET28b-MbTA containing the recombinant expression plasmid. The cells can be directly used as a biocatalyst or used for protein purification.

Example 4: Separation and Purification of Transaminase (MbTA)

The wet cells obtained in Example 3 were resuspended in a binding buffer (a 50 mM, pH 8.0 sodium phosphate buffer, containing 300 mM NaCl and 10 mM imidazole) and subjected to ultrasonication for cell disruption (in an ice bath, 240 W for 10 min, 2 s breaking, 2 s pause), the broken product was subjected to centrifugation at 12000 rpm for 40 min, the resulting supernatant was incubated with Ni affinity chromatography resin which had been equilibrated with the above-mentioned binding buffer, the resulting Ni affinity chromatography resin was washed with a washing buffer (a 50 mM, pH 8.0 sodium phosphate buffer containing 300 mM NaCl and 20 mM imidazole) until there were substantially no impurities, and then eluted with an elution buffer (a 50 mM, pH 8.0 sodium phosphate buffer, containing 300 mM NaCl and 250 mM imidazole), and the resulting eluate was collected to obtain solutions containing the target protein, the purity was identified by electrophoresis, and the solutions containing the target protein were combined and dialyzed with a dialysis buffer (a 50 mM, pH 8.0 sodium phosphate buffer) for 48 h (the MWCO of the dialysis bag is 141(D), and the retention was collected to obtain the purified transaminase. The protein content was determined to be 1.8 mg/mL by the Coomassie Brilliant Blue method, and the enzyme solution (enzyme activity was about 150 U/mg) was diluted with a 50 mM, pH 8.0 sodium phosphate buffer to a final concentration of 0.5 mg/mL, divided and stored at 80° C.

One unit of enzyme activity represented by U is defined as the amount of the transaminase MbTA required to produce 1 μmol product of the substrate [1-piperidinyl]-4[2,4, 5-trifluorophenyl]-1,3-butanedione per hour.

Example 5: Establishment of MbTA Gene Mutant Library

The plasmid pET28b-MbTA constructed in Example 2 was used as a template to carry out error-prone PCR with primer 1 (ATGGGCATCGATACC, SEQ ID NO: 5) and primer 2 (GTAGCAGATATCTTCGA, SEQ ID NO: 6). The PCR reaction mixture (total volume 50 μL) was composed of 5 μL of 10×Pfu DNA Polymerase Buffer, 1 μL of 10 mM dNTP mixture (dATP, dCTP, dGTP and dTTP each 2.5 mM), 0.5 μL of each of 50 μM cloning primer 1 and 50 μM cloning primer 2, 0.8 ng/μL plasmid template DNA, 2.5 U Taq DNA Polymerase, 0.2 mM $MnCl_2$ and deionized water to a final volume of 50 μL. A BioRad PCR instrument was used. The PCR reaction conditions were as follows: pre-denaturation at 95° C. for 5 min, a total of 30 cycles of denaturation at 95° C. for 30 s, annealing at 65° C. for 45 s and extension at 72° C. for 1 min, and a final extension at 72° C. for 10 min. After purification, the error-prone PCR product was used as primer, and the plasmid pET28b-MbTA constructed in Example 2 was used as a template to carry out megaprimer per to obtain megaprimer per product (ie. mutant library 1). The PCR reaction mixture comprised long/μL megaprimer, 1 ng/μL plasmid template and 2.5 U Pfu DNA Polymerase. The PCR reaction conditions were as follows: removal of A-tail at 72° C. for 5 min, pre-denaturation at 96° C. for 5 min, a total of 25 cycles of denaturation at 95° C. for 30 s, annealing at 60° C. for 45 s and extension at 72° C. for 4 min, and a final extension at 72° C. for 10 min.

Example 6: Screen MbTA Gene Mutant Library 1 to Obtain Mutant 1

The gene library 1 obtained in Example 5 was transformed into *Escherichia coli* BL21 (DE3) competent cells, and the transformation conditions were as follows: heat shock at 42° C. for 90 seconds. 9501 monoclones were picked from an LB plate containing 50 μg/mL kanamycin and respectively inoculated into LB medium containing 50 μg/ml kanamycin for induction expression and the induction conditions were the same as in Example 3, thereby obtaining wet cells of 9501 recombinant *Escherichia coli* strains containing mutant gene, ie. wet cells of mutant 1.

After obtaining the *Escherichia coli* containing the mutant protein, the biotransformation of a sitagliptin intermediate precursor ketone at a low concentration of 20 g/L was carried out to screen the strains. A reaction solution (15 ml) was composed of the following components with final concentrations: 0.75 g of wet cells of mutant 1, a pH 8-8.5 triethanolamine buffer, 20 g/L substrate (the sitagliptin intermediate precursor ketone [1-piperidinyl]-4-[2,4,5-trifluorophenyl]-1,3-butanedione), 10% (v/v) DMSO, 0.5 g/L pyridoxal phosphate and 10 g/L isopropylamine. The reaction conditions were as follows: 35° C. and 150 r/min for 36 h. Under the same conditions, a reaction solution without cells was used as a blank, and a reaction solution comprising wet cells of *Escherichia coli* BL21/pET28b containing an empty vector instead of the wet cells of mutant 1 was used as a negative control. After the reaction, sampling was carried out for HPLC detection (the conditions were the same as in Example 15) (50:50 acetonitrile:water, 10 mM ammonium acetate, a flow rate of 0.8 mL/min, a detection wavelength of 205 nm), and the mutant pET28b-MbTAmut1 which resulted in the highest conversion rate of the substrate was selected from 6503 proteins, and the highest conversion rate was 96% and the e.e. value was 99%. The nucleotide sequence and the amino acid sequence of the mutant pET28b-MbTAmut1 are shown in SEQ ID No: 3 and SEQ ID No: 4 of the sequence listing, respectively. Mutant 1 was obtained by substitution of tyrosine with proline at position 74, substitution of glutamic acid with aspartic acid at position 228, substitution of leucine with alanine at position 254 and substitution of methionine with threonine at position 290 of the amino acid sequence shown in SEQ ID NO: 2.

The wet cells of mutant 1 were obtained by the method in Example 3, and the purified enzyme of mutant 1 was obtained by the method in Example 4 (enzyme activity was about 150 U/mg).

Example 7: Application of Recombinant Transaminase MbTA in Preparation of Sitagliptin Intermediate (R)-3-amino-1-(1-piperidinyl)-4-(2,4,5-trifluorophenyl)-1-butanone The wet cells of the recombinant *Escherichia coli* BL21/pET28b-MbTA containing the expression recombinant plasmid obtained by the method in Example 3 or the purified MbTA enzyme obtained by the method in Example 4 as a biocatalyst and the sitagliptin intermediate precursor ketone [1-piperidinyl]-4-[2,4,5-trifluorophenyl]-1,3-butanedione as a substrate were used to carry out a biocatalytic reaction to synthesize a sitagliptin intermediate (R)-3-amino-1-(1-piperidinyl)-4-(2,4,5-trifluorophenyl)-1-butanone.

A reaction solution with a low substrate concentration (15 ml) was composed of the following components: 0.75 g of wet cells or 1 mg of purified enzyme of MbTA, a pH 8-8.5 triethanolamine buffer, 20 g/L substrate (the sitagliptin intermediate precursor ketone), 10% (v/v) DMSO, 0.5 g/L pyridoxal phosphate and 10 g/L isopropylamine. The reaction conditions were as follows: 35° C. and 150 r/min for 36 h. Under the same conditions, a reaction solution without cells was used as a blank, and a reaction solution with wet cells of *Escherichia coli* BL21/pET28b instead of the *Escherichia coli* BL21/pET28b-MbTA was used as a negative control. After the reaction, sampling was carried out for HPLC detection (the conditions were the same as in Example 15), the conversion rate was 2.3% and the e.e. value was 99%. And when the reaction was carried out with the *Escherichia coli* containing no transaminase MbTA as the catalyst and under the same conditions, the substrate conversion rate was less than 0.01%.

A reaction solution with a high substrate concentration (15 ml) was composed of the following components: 0.75 g of wet cells or 1 mg of purified enzyme of MbTA, a pH 8-8.5 triethanolamine buffer, 50 g/L substrate (the sitagliptin intermediate precursor ketone), 40% (v/v) DMSO, 0.5 g/L pyridoxal phosphate and 10 g/L isopropylamine. The reaction conditions were as follows: 35° C. and 150 r/min for 36 h. Under the same conditions, a reaction solution without cells was used as a blank, and a reaction solution with wet cells of *Escherichia coli* BL21/pET28b instead of the *Escherichia coli* BL21/pET28b-MbTA was used as a negative control. After the reaction, sampling was carried out for HPLC detection (the conditions were the same as in Example 15), and the substrate conversion rate was less than 1%. And when the reaction was carried out with the *Escherichia coli* containing no transaminase MbTA as the catalyst and under the same conditions, the substrate conversion rate was less than 0.01%.

Example 8: Application of Recombinant Transaminase MbTA Mutant 1 in Preparation of a Sitagliptin Intermediate (R)-3-amino-1-(1-piperidinyl)-4-(2,4,5-trifluorophenyl)-1-butanone The wet cells of the recombinant *Escherichia coli* BL21/pET28b-MbTAmut1 containing the expression recombinant plasmid in Example 6 obtained by the method in Example 3 or the purified enzyme of MbTA mutant 1 obtained by the method in Example 4 as a biocatalyst and the sitagliptin intermediate precursor ketone [1-piperidinyl]-4-[2,4,5-trifluorophenyl]-1,3-butanedione as a substrate were used to carry out a biocatalytic reaction to synthesize a sitagliptin intermediate
(R)-3-amino-1-(1-piperidinyl)-4-(2,4,5-trifluorophenyl)-1-butanone.

A reaction solution with a low substrate concentration (15 ml) was composed of the following components: 0.75 g of wet cells or 1 mg of purified enzyme of MbTA, a pH 8-8.5 triethanolamine buffer, 2 g/L substrate (the sitagliptin intermediate precursor ketone), 10% (v/v) DMSO, 0.5 g/L pyridoxal phosphate and 10 g/L isopropylamine. The reaction conditions were as follows: 35° C. and 150 r/min for 36 h. Under the same conditions, a reaction solution without cells was used as a blank, and a reaction solution with wet cells of *Escherichia coli* BL21/pET28b instead of the *Escherichia coli* BL21/pET28b-MbTAmut1 was used as a negative control. After the reaction, sampling was carried out for HPLC detection (the conditions were the same as in Example 15), the conversion rate was 95.5% and the e.e. value was 99% at the substrate concentration of 2 g/L. And when the reaction was carried out with the *Escherichia coli* containing no transaminase MbTA mut1 as the catalyst and under the same conditions, the substrate conversion rate was less than 0.01%.

A reaction solution with a high substrate concentration (15 ml) was composed of the following components: 0.75 g of wet cells or 1 mg of purified enzyme of MbTA mutant 1, a pH 8-8.5 triethanolamine buffer, 50 g/L substrate the sitagliptin intermediate precursor ketone, 40% (v/v) DMSO, 0.5 g/L pyridoxal phosphate and 10 g/L isopropylamine. The reaction conditions were as follows: 35° C. and 150 r/min for 36 h. Under the same conditions, a reaction solution without cells was used as a blank, and a reaction solution with wet cells of *Escherichia coli* BL21/pET28b instead of the *Escherichia coli* BL21/pET28b-MbTAmut1 was used as a negative control. After the reaction, sampling was carried out for HPLC detection (the conditions were the same as in Example 15), the substrate conversion rate was 58% and the e.e. value was 99%. And when the reaction was carried out with the *Escherichia coli* containing no transaminase MbTA mut1 as the catalyst and under the same conditions, the substrate conversion rate was less than 0.01%.

Further, Examples 9-14 introduced an application of the recombinant transaminase MbTA mutant 1 in preparation of sitagliptin ester intermediates.

Example 9: Application of the Recombinant Transaminase MbTA Mutant 1 in Preparation of (R)-3-amino-4-(2,4,5-trifluorophenyl)-butyric acid methyl ester The wet cells of the recombinant *Escherichia coli* BL21/pET28b-MbTAmut1 containing the expression recombinant plasmid in Example 6 obtained by the method in Example 3 as a biocatalyst and 3-carbonyl-4-(2,4,5-trifluorophenyl)-butyric acid methyl ester as a substrate were used to carry out a biocatalytic reaction to synthesize (R)-3-amino-4-(2,4,5-trifluorophenyl)-butyric acid methyl ester.

A reaction solution (15 ml) was composed of the following components with final concentrations: 0.75 g of the wet cells, a pH 8-8.5 triethanolamine buffer, 20 g/L substrate (3-carbonyl-4-(2,4,5-trifluorophenyl)-butyric acid methyl ester), 20% (v/v) DMSO, 0.5 g/L pyridoxal phosphate and 10 g/L isopropylamine. The reaction conditions were as follows: 35° C. and 150 r/min for 36 h. Under the same conditions, a reaction solution without cells was used as a blank, and a reaction solution with wet cells of *Escherichia coli* BL21/pET28b containing an empty vector instead of *Escherichia coli* BL21/pET28b-MbTAmut1 was used as a negative control. After the reaction, sampling was carried out for HPLC detection (the conditions were the same as in Example 15), about 0.12 mol of (R)-3-amino-4-(2,4,5-trifluorophenyl)-butyric acid methyl ester (28.3 g) was obtained from 0.12 mol of the substrate (3-carbonyl-4-(2,4,5-trifluorophenyl)-butyric acid methyl ester), the substrate conversion rate was 90% and the e.e. value was 99%. And when the reaction was carried out with the *Escherichia coli* containing no transaminase MbTA mut1 as the catalyst and under the same conditions, the substrate conversion rate was less than 0.01%.

Example 10: Application of the Recombinant Transaminase MbTA Mutant 1 in Preparation of (R)-3-amino-4-(2,4,5-trifluorophenyl)-butyric acid ethyl ester The wet cells of the recombinant *Escherichia coli* BL21/pET28b-MbTAmut1 containing the expression recombinant plasmid in Example 6 obtained by the method in Example 3 as a biocatalyst and 3-carbonyl-4-(2,4,5-trifluorophenyl)-butyric acid ethyl ester as a substrate were used to carry out a biocatalytic reaction to synthesize (R)-3-amino-4-(2,4,5-trifluorophenyl)-butyric acid ethyl ester.

A reaction solution (15 ml) was composed of the following components with final concentrations: 0.75 g of the wet cells, a pH 8-8.5 triethanolamine buffer, 20 g/L substrate (3-carbonyl-4-(2,4,5-trifluorophenyl)-butyric acid ethyl ester), 20% (v/v) DMSO, 0.5 g/L pyridoxal phosphate and 10 g/L isopropylamine. The reaction conditions were as follows: 35° C. and 150 r/min for 36 h. Under the same conditions, a reaction solution without cells was used as a blank, and a reaction solution with wet cells of *Escherichia coli* BL21/pET28b containing an empty vector instead of *Escherichia coli* BL21/pET28b-MbTAmut1 was used as a negative control. After the reaction, sampling was carried out for HPLC detection (the conditions were the same as in Example 15), the substrate conversion rate was 90% and the e.e. value was 99%. And when the reaction was carried out with the *Escherichia coli* containing no transaminase MbTA mut1 as the catalyst and under the same conditions, the substrate conversion rate was less than 0.01%.

Example 11: Application of the Recombinant Transaminase MbTA Mutant 1 in Preparation of (R)-3-amino-4-(2,4,5-trifluorophenyl)-butyric acid propyl ester The wet cells of the recombinant *Escherichia coli* BL21/pET28b-MbTAmut1 containing the expression recombinant plasmid in Example 6 obtained by the method in Example 3 as a biocatalyst and 3-carbonyl-4-(2,4,5-trifluorophenyl)-butyric acid propyl ester as a substrate were used to carry out a biocatalytic reaction to synthesize (R)-3-amino-4-(2,4,5-trifluorophenyl)-butyric acid propyl ester.

A reaction solution (15 ml) was composed of the following components with final concentrations: 0.75 g of the wet cells, a pH 8-8.5 triethanolamine buffer, 20 g/L substrate (3-carbonyl-4-(2,4,5-trifluorophenyl)-butyric acid propyl ester), 20% (v/v) DMSO, 0.5 g/L pyridoxal phosphate and 10 g/L isopropylamine. The reaction conditions were as follows: 35° C. and 150 r/min for 36 h. Under the same conditions, a reaction solution without cells was used as a blank, and a reaction solution with wet cells of *Escherichia coli* BL21/pET28b containing an empty vector instead of *Escherichia coli* BL21/pET28b-MbTAmut1 was used as a negative control. After the reaction, sampling was carried out for HPLC detection (the conditions were the same as in Example 15), the substrate conversion rate was 88% and the e.e. value was 99%. And when the reaction was carried out with the *Escherichia coli* containing no transaminase MbTA mut1 as the catalyst and under the same conditions, the substrate conversion rate was less than 0.01%.

Example 12: Application of the Recombinant Transaminase MbTA Mutant 1 in Preparation of (R)-3-amino-4-(2,4,5-trifluorophenyl)-butyric acid isopropyl ester The wet cells of the recombinant *Escherichia coli* BL21/pET28b-MbTAmut1 containing the expression recombinant plasmid in Example 6 obtained by the method in Example 3 as a biocatalyst and 3-carbonyl-4-(2,4,5-trifluorophenyl)-butyric acid isopropyl ester as a substrate were used to carry out a biocatalytic reaction to synthesize (R)-3-amino-4-(2,4,5-trifluorophenyl)-butyric acid isopropyl ester.

A reaction solution (15 ml) was composed of the following components with final concentrations: 0.75 g of the wet cells, a pH 8-8.5 triethanolamine buffer, 20 g/L substrate (3-carbonyl-4-(2,4,5-trifluorophenyl)-butyric acid isopropyl ester), 20% (v/v) DMSO, 0.5 g/L pyridoxal phosphate and 10 g/L isopropylamine. The reaction conditions were as follows: 35° C. and 150 r/min for 36 h. Under the same conditions, a reaction solution without cells was used as a blank, and a reaction solution with wet cells of *Escherichia coli* BL21/pET28b containing an empty vector instead of *Escherichia coli* BL21/pET28b-MbTAmut1 was used as a negative control. After the reaction, sampling was carried out for HPLC detection (the conditions were the same as in Example 15), the substrate conversion rate was 84% and the e.e. value was 99%. And when the reaction was carried out with the *Escherichia coli* containing no transaminase MbTA mut1 as the catalyst and under the same conditions, the substrate conversion rate as the catalyst was less than 0.01%.

Example 13: Application of the Recombinant Transaminase MbTA Mutant 1 in Preparation of (R)-3-amino-4-(2,4,5-trifluorophenyl)-butyric acid isobutyl ester The wet cells of the recombinant *Escherichia coli* BL21/pET28b-MbTAmut1 containing the expression recombinant plasmid in Example 6 obtained by the method in Example 3 as a biocatalyst and 3-carbonyl-4-(2,4,5-trifluorophenyl)-butyric acid isobutyl ester as a substrate were used to carry out a biocatalytic reaction to synthesize (R)-3-amino-4-(2,4,5-trifluorophenyl)-butyric acid isobutyl ester.

A reaction solution (15 ml) was composed of the following components with final concentrations: 0.75 g of the wet cells, a pH 8-8.5 triethanolamine buffer, 20 g/L substrate (3-carbonyl-4-(2,4,5-trifluorophenyl)-butyric acid isobutyl ester), 20% (v/v) DMSO, 0.5 g/L pyridoxal phosphate and 10 g/L isopropylamine. The reaction conditions were as follows: 35° C. and 150 r/min for 36 h. The enzyme was verified to be high selective to prepare (R)-3-amino-4-(2,4,5-trifluorophenyl)-butyric acid isobutyl ester by transamination. Under the same conditions, a reaction solution without cells was used as a blank, and a reaction solution with wet cells of *Escherichia coli* BL21/pET28b containing an empty vector instead of *Escherichia coli* BL21/pET28b-MbTAmut1 was used as a negative control. After the reaction, sampling was carried out for HPLC detection (the conditions were the same as in Example 15), the substrate conversion rate was 86% and the e.e. value was 99%. And when the reaction was carried out with the *Escherichia coli* containing no transaminase MbTA mut1 as the catalyst and under the same conditions, the substrate conversion rate was less than 0.01%.

Example 14: Application of the Recombinant Transaminase MbTA Mutant 1 in Preparation of (R)-3-amino-4-(2,4,5-trifluorophenyl)-butyric acid benzyl ester The wet cells of the recombinant *Escherichia coli* BL21/pET28b-MbTAmut1 containing the expression recombinant plasmid in Example 6 obtained by the method in Example 3 as a biocatalyst and 3-carbonyl-4-(2,4,5-trifluorophenyl)-butyric acid benzyl ester as a substrate were used to carry out a biocatalytic reaction to synthesize (R)-3-amino-4-(2,4,5-trifluorophenyl)-butyric acid benzyl ester.

A reaction solution (15 ml) was composed of the following components with final concentrations: 0.75 g of the wet cells, a pH 8-8.5 triethanolamine buffer, 20 g/L substrate (3-carbonyl-4-(2,4,5-trifluorophenyl)-butyric acid benzyl ester), 20% (v/v) DMSO, 0.5 g/L pyridoxal phosphate and 10 g/L isopropylamine. The reaction conditions were as follows: 35° C. and 150 r/min for 36 h. Under the same conditions, a reaction solution without cells was used as a blank, and a reaction solution with wet cells of *Escherichia coli* BL21/pET28b containing an empty vector instead of *Escherichia coli* BL21/pET28b-MbTAmut1 was used as a negative control. After the reaction, sampling was carried out for HPLC detection (the conditions were the same as in Example 15), the substrate conversion rate was 84% and the e.e. value was 99%. And when the reaction was carried out with the *Escherichia coli* containing no transaminase MbTA mut1 as the catalyst and under the same conditions, the substrate conversion rate was less than 0.01%.

Example 15: Liquid Phase Detection Method of Sitagliptin Intermediate Precursor Ketone, Sitagliptin (R)-Intermediate and (S)-Enantiomer of Sitagliptin HPLC instrument: Shimadzu LC-16 system-SPD-16 UV detector and Hitachi 8DD-0801 system-1410 UV detector.

The conversion rate was detected by a chromatographic column ZORBAX Eclipse XDB-C18 (4.6 mm×250 mm, Sum), the mobile phase was water:acetonitrile=50:50 (v/v), and 10 mM ammonium acetate was added to the water phase, the flow rate was 0.8 mL/min, The column temperature was 40° C., and the detection wavelength was 205 nm. The retention time of sitagliptin intermediate precursor ketone was 4.0 min. The retention time of each sitagliptin intermediate was 2.8 min.

The e.e. was detected by a chiral chromatography column Chiralpak AD-H (150×4.6 mm, 5 μm), the mobile phase was ethanol/n-heptane/diethylamine=60:40:0.1 (v/v/v), and the flow rate was 0.8 mL/min, the column temperature was 35° C., the detection wavelength was 205 nm. The retention times of sitagliptin intermediate precursor ketone and sitagliptin intermediate (R) enantiomer were about 10 and 5 min, respectively. The retention time of the (S)-enantiomer of the sitagliptin intermediate was 9.5 min. (The liquid phase was detected by Shimadzu LC-20AD system-SPD20A detector)

Product e.e.$_p$ is calculated as follows:

$$e.e._p = (C_R - C_S)/(C_R + C_S) \times 100\%$$

$C_R$ is the peak area of sitagliptin and $C_S$ is the peak area of its S-enantiomer.

Example 16: Separation and Purification of High-Purity Sitagliptin Intermediate (R)-3-amino-1-(1-piperidinyl)-4-(2,4,5-trifluorophenyl)-1-butanone from the Reaction System 400 mL of the reaction solution with low substrate concentration in Example 8 was adjusted to pH1.5 with concentrated hydrochloric acid (the mass fraction was 36%-38%), 72 g of diatomaceous earth (the median particle size was 19.6 μm) was added to adsorb cells and the resulting mixture was stirred for 20 min. The mixture was subjected to suction filtration to obtain filtrate a and filtration residue a, 600 mL of 1M hydrochloric acid was added to the filtration residue a, the mixture was stirred for 20 min and subjected to suction filtration, thereby obtaining filtrate b and filtration residue b; the filtrate a and the filtrate b were mixed to obtain a total volume of about 1.0 L, the mixed filtrate was subjected to extraction once with 500 mL of dichloromethane (purity 99.5%) to obtain aqueous phase a and organic phase a, the organic phase a was subjected to extraction with 100 mL of 1M hydrochloric acid to obtain aqueous phase b and organic phase b, the aqueous phase a and the aqueous phase b were mixed and adjusted to pH12 with sodium hydroxide, added with 1.2 L of dichloromethane for extraction to obtain organic phase c and aqueous phase c. The aqueous phase c was added with 800 mL of dichloromethane for extraction to obtain aqueous phase d and organic phase d. The organic phase c and the organic phase d were mixed, washed twice with a saturated sodium chloride aqueous solution, dried with anhydrous sodium sulfate, subjected to suction filtration to remove sodium sulfate and subjected to rotary evaporation at 45° C., thereby obtaining 20.5 g of white powder. After the liquid phase detection in Example 15, the yield was 93%, and the purity of the sitagliptin intermediate was 99.5%. The overall yield of the sitagliptin intermediate was 82%.

It should be understood that after reading the above content of the present invention, a person skilled in the art can make various changes or modifications to the present invention, and that these equivalent forms are also involved in the scope defined by appending claims of the present application.

The invention claimed is:

1. A transaminase mutant, wherein the transaminase mutant is obtained by substitution of tyrosine with proline at position 74, substitution of glutamic acid with aspartic acid at position 228, substitution of leucine with alanine at position 254 and substitution of methionine with threonine at position 290 of the amino acid sequence shown in SEQ ID NO: 2.

2. An encoding gene of the transaminase mutant as claimed in claim 1, wherein the nucleotide sequence of the encoding gene is shown in SEQ ID NO: 3.

3. A recombinant genetically engineered strain transformed by the encoding gene of the transaminase mutant as claimed in claim 2.

4. A method for biocatalytic synthesis of a sitagliptin intermediate from a sitagliptin precursor ketone using the transaminase mutant as claimed in claim 1 in the presence of the transaminase mutant of claim 1, wherein the method comprises:

constructing a reaction system comprising wet cells or a purified transaminase as a biocatalyst, [1-piperidinyl]-4-[2,4,5-trifluorophenyl]-1,3-butanedione as a substrate, dimethyl sulfoxide as a cosolvent, pyridoxal phosphate as a coenzyme, isopropyl amine as a cosubstrate, and a pH 8-9 triethanolamine buffer as a reaction medium; and carrying out a biocatalytic reaction is carried out at 30-45° C. and 100-250 r/min, after the reaction is completed, subjecting the reaction solution to separation and purification to obtain (R)-3-amino-I-(I-piperidinyl)-4-(2,4, 5-trifluorophenyl)-I-butanone, wherein the wet cells are obtained by fermentation culture of a recombinant genetically engineered bacterium bacteria containing an encoding gene encoding the of a transaminase mutant and the purified transaminase is obtained by subjecting the wet cells to ultrasonication and then extraction.

5. The method as claimed in claim 4, wherein in the reaction system, an amount of the wet cells is 10-100 g/L, an amount of the purified transaminase is 0.01-1.0 g/L, a final concentration of the substrate is 2-50 g/L, a final concentration of dimethyl sulfoxide is 10-40% (v/v), a final concentration of pyridoxal phosphate is 0.5 g/L, and a final concentration of isopropyl amine is 10 g/L.

6. A method for biocatalytic synthesis of a sitagliptin ester intermediate from a prochiral carbonyl compound in the presence of the transaminase mutant as claimed in claim 1, the method comprising reacting the prochiral compound in the presence of the transaminase and an amino donor to produce the sitagliptin ester intermediate, wherein the prochiral carbonyl compound is one selected from the group consisting of the following compounds: 3-carbonyl-4-(2,4, 5-trifluorophenyl)-butyric acid methyl ester, 3-carbonyl-4-(2,4,5-Trifluorophenyl)-butyric acid propyl ester, 3-carbonyl-4-(2,4,5-trifluorophenyl)-butyric acid isopropyl ester, 3-carbonyl-4-(2,4,5-trifluorophenyl)-butyric acid ethyl ester, 3-carbonyl-4-(2,4,5-trifluorophenyl)-butyric acid isobutyl ester and 3-carbonyl-4 (2,4,5-trifluorophenyl) butyric acid benzyl ester.

7. The method as claimed in claim 6, wherein the method comprises:
   constructing a reaction solution system comprising wet cells as a biocatalyst, the prochiral carbonyl compound as a substrate, dimethyl sulfoxide as a cosolvent, pyridoxal phosphate as a coenzyme, isopropyl amine as a cosubstrate, and a pH 8-9 triethanolamine buffer as a reaction medium; and
   carrying out a biocatalytic reaction at 25-35° C. and 100-250 r/min, after the reaction is completed, subjecting the reaction solution to separation and purification to obtain the sitagliptin ester intermediate; in which, the wet cells are obtained by a fermentation culture of a recombinant genetically engineered bacterium bacteria containing an encoding gene encoding the transaminase mutant.

8. The method as claimed in claim 7, wherein in the reaction system, an amount of the wet cells is 10-100 g/L, a final concentration of the substrate is 2-60 g/L, a final concentration of dimethyl sulfoxide is 10-40% (v/v), a final concentration of pyridoxal phosphate is 0.5 g/L, and a final concentration of isopropyl amine is 10 g/L.

9. The method as claimed in claim 4, wherein the wet cells are prepared as follows: the recombinant *Escherichia coli* genetically engineered bacterium strain containing the encoding gene of the transaminase mutant is inoculated into LB liquid medium containing 50 μg/ml kanamycin, cultured at 37° C. and 200 rpm for 12 hours to produce an inoculum, the resulting inoculum is inoculated at a 1% volume into fresh LB liquid medium containing 50 μg/ml kanamycin with 1% incubating volume and cultured at 37° C. and 150 rpm to produce a culture; when OD600 of the culture reaches 0.6-0.8, IPTG is added with a final concentration of 0.1 mM, and the culture bacteria solution is subjected to induction culture at 28° C. for 12 hours to produce a resulting solution; the resulting solution is subjected to centrifugation at 4° C. and 5000 rpm for 20 min to produce a supernatant and sediment, the resulting supernatant is discarded and the sediment is collected, thereby obtaining the wet cells.

* * * * *